United States Patent
Revelant et al.

(10) Patent No.: US 10,202,328 B2
(45) Date of Patent: Feb. 12, 2019

(54) OPTIMIZED PROCESS FOR EXTRACTION OF FERULIC ACID WITH PRETREATMENT

(71) Applicant: RHODIA OPERATIONS, Paris (FR)

(72) Inventors: Denis Revelant, Genas (FR); Stephanie Foucher, Meyzieu (FR); Dominique Horbez, Franconville (FR); Philippe Marion, Vernaison (FR)

(73) Assignee: Rhodia Operations, Paris (FR)

( * ) Notice: Subject to any disclaimer, the term of this patent is extended or adjusted under 35 U.S.C. 154(b) by 0 days.

(21) Appl. No.: 14/892,790

(22) PCT Filed: May 19, 2014

(86) PCT No.: PCT/EP2014/060259
§ 371 (c)(1),
(2) Date: Nov. 20, 2015

(87) PCT Pub. No.: WO2014/187784
PCT Pub. Date: Nov. 27, 2014

(65) Prior Publication Data
US 2016/0145183 A1 May 26, 2016

(30) Foreign Application Priority Data

May 21, 2013 (FR) ..................................... 13 54533
Sep. 5, 2013 (FR) ..................................... 13 02058

(51) Int. Cl.
| | | |
|---|---|---|
| C07C 51/47 | (2006.01) | |
| C07C 51/00 | (2006.01) | |
| C07C 51/43 | (2006.01) | |
| C07C 51/48 | (2006.01) | |
| C12P 7/62 | (2006.01) | |

(52) U.S. Cl.
CPC .............. *C07C 51/47* (2013.01); *C07C 51/00* (2013.01); *C07C 51/43* (2013.01); *C07C 51/48* (2013.01); *C12P 7/62* (2013.01)

(58) Field of Classification Search
CPC ......... C07C 51/09; C07C 59/64; C07C 51/47; C07C 51/00; C07C 51/43; C07C 51/48; C07C 51/36; C07C 55/14; C12P 7/24; C12P 19/04; C12P 7/42; C12P 7/62; C12R 1/01; Y10S 435/822; G01N 2035/00326; G01N 2035/00495; G01N 35/0092; G01N 35/026; G01N 35/10; G01N 35/00871; G01N 2015/1006; G01N 35/1065; G01N 21/25; G01N 15/1475; G01N 2035/00138; G01N 2035/00356; G01N 2035/00366; A23L 33/105; A23L 7/107; A23L 7/115; C08B 30/10; C08B 37/0057; A61K 2800/10; A61K 47/12; A61K 47/183; A61K 47/32; A61K 8/042; A61K 8/361; A61K 8/37; A61K 8/64; A61K 8/08

See application file for complete search history.

(56) References Cited

U.S. PATENT DOCUMENTS

| | | | |
|---|---|---|---|
| 4,349,628 A * | 9/1982 | English ................. | B01D 3/143 202/180 |
| 5,288,902 A | 2/1994 | Taniguchi et al. | |
| 6,133,003 A | 10/2000 | Rabenhorst et al. | |
| 7,709,033 B2 * | 5/2010 | Kvist ...................... | A23D 9/00 426/49 |
| 9,872,907 B2 * | 1/2018 | Matsumoto .......... | A61K 47/183 |
| 2007/0118916 A1 * | 5/2007 | Puzio ................. | C12N 15/8214 800/278 |
| 2009/0171129 A1 * | 7/2009 | Evanko ................... | C07C 29/80 568/916 |
| 2010/0330633 A1 * | 12/2010 | Walther ................ | C12M 21/12 435/150 |
| 2015/0080220 A1 * | 3/2015 | Yao ....................... | A61K 47/36 504/358 |

FOREIGN PATENT DOCUMENTS

| | | |
|---|---|---|
| CN | 1425773 A | 6/2003 |
| CN | 102381962 A | 3/2012 |
| EP | 0761817 A2 | 8/1996 |
| EP | 0885968 A1 | 12/1998 |
| WO | WO 2001067891 A1 | 9/2001 |
| WO | WO 2004110975 A1 | 12/2004 |

OTHER PUBLICATIONS

Studies on extraction and purification of ferulic acid in wheat bran, Wang Bei, database of fulltext theses for master's degree, Engineering Science, vol. 1 No. 10, May 2012.

* cited by examiner

*Primary Examiner* — Deborah K Ware
(74) *Attorney, Agent, or Firm* — Osha Liang LLP

(57) ABSTRACT

A process for extraction of ferulic acid present in an aqueous phase, obtained by treatment of at least one plant material, and also containing polysaccharides, is described, said process comprising at least the following steps:

1) the treatment of said plant material followed by a solid/liquid separation to recover a solid phase and an aqueous liquid phase comprising the ferulic acid and said polysaccharides,
2) the treatment of said liquid phase to selectively separate, on the one hand, the polysaccharides and, on the other hand, the ferulic acid present in an aqueous fraction,
3) the concentration of said aqueous fraction containing the ferulic acid so as to recover a ferulic acid-concentrated stream,
4) the recovery of the ferulic acid in solid form.

17 Claims, 1 Drawing Sheet

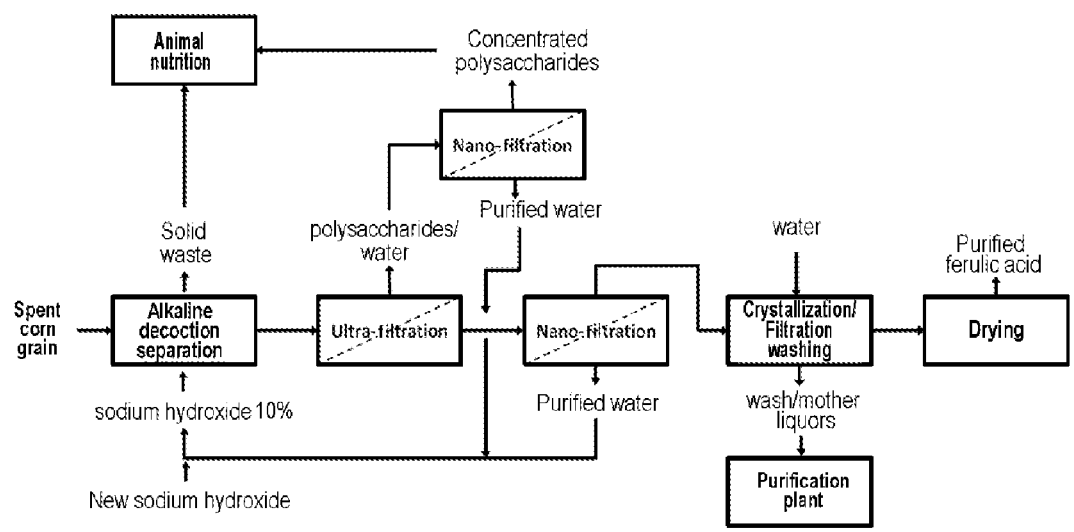

OPTIMIZED PROCESS FOR EXTRACTION OF FERULIC ACID WITH PRETREATMENT

This application is a U.S. national stage entry under 35 U.S.C. § 371 of International Patent Application No. PCT/EP2014/060259, filed May 19, 2014, which claims priority to French Patent Application Nos. FR 1354533, filed on May 21, 2013 and FR 1302058, filed on Sep. 5, 2013, the whole content of each of these applications is hereby incorporated herein by reference for all purposes.

The present invention relates to the field of the recovery of the natural ferulic acid present in an aqueous effluent obtained by treatment of plant material with a view to extracting it with a high purity in order to be able to use it as a raw material in various types of industry, in particular the chemical, cosmetics, pharmaceutical, biotechnology or food-processing industry. The present invention very advantageously finds an application for the preparation of flavorings from purified ferulic acid, in particular of food flavorings, in particular vanillin.

PRIOR ART

Ferulic acid is present in many seeds such as rice, wheat, corn or oats. It is also found in by-products of the food-processing industry, such as spent corn grain (starch manufacture), bagasse (conversion of sugarcane), beetroot pulp or the residue from refining rice bran oil, called soap stock. It is known practice to recover ferulic acid by extraction of wheat bran, rice bran or corn bran after alkaline cooking or enzymatic treatment. After separation of the residual solid plant material, a dilute aqueous stream made up of 80% to 99% by weight of water and also of ferulic acid, polysaccharides and mineral salts is obtained. U.S. Pat. No. 5,288,902 describes a process of alkaline cooking of the residue resulting from the refining of rice bran oil. The ferulic acid is purified by recrystallization after extraction of the impurities with hexane. Patent application WO 2004/110975 describes the direct treatment of the juice from cooking, with lime, of corn grain by carrying out in particular a step of acidification of said effluent, called nejayote, resulting from alkaline cooking and then a step of adsorption of the ferulic acid on a synthetic or activated-carbon resin, followed by elution with an organic solvent, and finally, a recrystallization step. Patent application WO 2001/067891 describes a pretreatment of rice bran by extrusion in the presence of water, followed by enzymatic hydrolysis in the presence of cellulase and/or of hemicellulase, such as mannases, glucanase or arabinases. The ferulic acid is extracted using an organic solvent, while the aqueous fraction is treated with an α-amylase in order to generate a fraction of soluble polysaccharides.

Generally, the processes described result in a considerable consumption of water with a very partial exploitation of the treatment co-products, in particular the residual plant material and the polysaccharides. The environmental impact is not optimized, thus contributing to a depletion of groundwater and to an increase in the organic load discharged into the environment. Furthermore, the presence of polysaccharides during the ferulic acid purification phase leads to a significant loss of yield and compromises the economic profitability of the process.

Thus, in order to remedy the drawbacks encountered with the implementation of the prior processes, the present invention proposes the implementation of a clean process for extraction of ferulic acid resulting in the production of ferulic acid with an improved purity and an increased yield.

The ferulic acid thus obtained is advantageously converted into natural vanillin by means of a biofermentation process.

DESCRIPTION OF THE INVENTION

A subject of the present invention is a process for extraction of ferulic acid present in an aqueous phase obtained by treatment of at least one plant material, and also containing polysaccharides, said process comprising at least the following steps:

1) the treatment of said plant material followed by a solid/liquid separation to recover a solid phase and an aqueous liquid phase comprising the ferulic acid and said polysaccharides, 2) the treatment of said liquid phase to selectively separate, on the one hand, the polysaccharides and, on the other hand, the ferulic acid present in an aqueous fraction, 3) optionally the concentration of said aqueous fraction containing the ferulic acid so as to recover a ferulic acid-concentrated stream, 4) the recovery of the ferulic acid in solid form.

In accordance with the process of the invention, when step 3) is carried out, the order of steps 2) and 3) is of no consequence once the treatment according to said step 1) has been carried out. Preferably, said step 2) precedes said step 3). Whatever the order of steps 2) and 3), the stream which is subjected to the recovery step according to said step 4) of the process of the invention is a stream which is concentrated in terms of ferulic acid and substantially depleted of polysaccharides, i.e. it contains less than 500 ppm, preferably less than 100 ppm, of polysaccharides.

In accordance with the invention, the step of selective separation of the polysaccharides and the step of concentration of the aqueous fraction containing the ferulic acid are steps of pretreatment of said aqueous phase, obtained at the end of said step 1), which are carried out before proceeding with the recovery of the actual ferulic acid according to said step 4).

The plant material used in the process of the invention is advantageously selected from wheat bran, rice bran, corn bran, oat bran, spent corn grains, bagasse, beetroot pulp and the residue from refining rice bran oil, and mixtures thereof. Advantageously, said plant material is selected from wheat bran, rice bran, corn bran and spent corn grain.

The treatment of said plant material according to said step 1) of the process of the invention consists in subjecting the plant material to an alkaline decoction and/or to an enzymatic treatment so as to release the chemical species constituting or linked to the cellulose or the hemicellulose of the starting plant. In particular, the treatment according to said step 1) releases the ferulic acid and the polysaccharides. Preferably, said treatment according to said step 1) consists at least of the alkaline cooking or decoction of at least one of the raw plant materials mentioned above. The treatment by alkaline decoction does not cause any structural modification of the initial chemical species, it is simply a release by hydrolysis of specific functions, in particular ester bridges. Within the meaning of the European Directive (Regulation (EC) No. 1334/2008 of the European Parliament and of the Council of Dec. 16, 2008), such a physical treatment makes it possible to preserve the criteria of natural nature of the compounds released, namely the ferulic acid and the polysaccharides.

The treatment by alkaline decoction (step 1) consists in macerating and cooking said plant material in an alkaline solution or an alkaline suspension. The plant material/alkaline solution weight ratio is between 0.05 and 0.5. The content of base in the alkaline solution is between 1% and 30% by weight. The base used for this treatment is advantageously selected from sodium hydroxide, potassium hydroxide and sodium carbonate. The temperature at which the alkaline decoction is carried out is preferentially between 60 and 120° C. The operating time of this treatment is preferentially between 2 and 8 hours. The alkaline decoction is advantageously carried out using a stirred tank equipped with a stirring spindle, a heating jacket and counter-paddles making it possible to optimize the material and energy transfer conditions. The raw plant material is introduced into said tank containing a dilute alkaline solution. At the end of the decoction, the mixture obtained is a two-phase mixture: the solid phase contains constituent cellulose and hemicellulose fibers of the plant cell walls, while the liquid phase contains dissolved polysaccharides, elementary sugars, mineral salts, proteins and salified ferulic acid.

Preferably, the quality of the material transfer in the alkaline decoction step is optimized using technologies with a high shear coefficient ($>5000$ s$^{-1}$) coupling efficient energy transfer and bringing of the mixture constituents into contact. Among these technologies, mention may particularly be made of twin-screw extruders and grinder-homogenizers. They have the advantage of minimizing the amounts of solvent and can be implemented in successive or parallel steps. For example, in the twin-screw extruder, it is possible to continuously feed the plant material to be treated and the alkaline solution by finely controlling the flow rates, temperature and arrangement of the internal screw threads (conveying, blending and/or counter-screw). The fine control of the various parameters is carried out according to a practice known to those skilled in the art. The twin-screw extruders can be equipped with a washing zone in which the extrudate is continuously diluted with a stream of washing water so as to allow easier subsequent separation of the residual solid fibers and of the liquid alkaline phase containing the polysaccharides and the salified ferulic acid having been dissolved. It is also advantageous to equip the extruder, especially the twin-screw extruder, with a sheath filter in order to carry out the subsequent solid/liquid separation in situ.

The technologies using grinder-homogenizers are also advantageous for dilacerating the plant fibers and thus facilitating the contact with the alkaline solution. They can be implemented in batchwise mode or in continuous mode. For example, grinders of Ultra Turrax® or FRYMA® type can be exploited. These grinders can be used while being immersed in the alkaline solution or can be controlled online. An online grinder and a stirred tank can in particular be coupled so as to have a sufficient residence time (for example 2 to 8 hours of alkaline decoction) and an intensification of the contact between plant fibers and alkaline solution.

It is also advantageous to couple a technology having a high shear coefficient with a technology using microwave irradiation or ultrasonic waves, which can further exacerbate the release of ferulic acid by locally accelerating the hydrolysis kinetics.

The treatment of said plant material according to said step 1) of the process of the invention can also consist of an enzymatic treatment. The enzymes perform a release of the ferulic acid and of the polysaccharides by hydrolysis of specific functions, in particular of the constituent ester functions of the plant wall. Said enzymes are preferentially selected from cellulase, hemicellulase and feruloyl esterase, and mixtures thereof. Said enzymes are commercially available. The enzymatic treatment is advantageously carried out at a temperature of between 20° C. and 70° C., for a period of between 0.5 and 20 hours. It is advantageous to couple the alkaline decoction described above with an enzymatic treatment in order to maximize the release of ferulic acid (alkaline-enzymatic decoction). It is also advantageous to couple the enzymatic treatment with an implementation by extrusion (enzymatic extrusion).

Preferably, said treatment of plant material according to said step 1) of the process according to the invention consists of an alkaline decoction or of an alkaline-enzymatic decoction.

The solid/liquid separation step combined with the plant material treatment step, preferentially with the alkaline decoction step, is for example implemented by centrifugation or by filtration. The implementation by centrifugation is advantageously carried out using a plate centrifuge or centrifugal decanter allowing continuous separation of the solid and liquid phases. The solid phase harvested at the end of the solid/liquid separation step contains constituent cellulose fibers and hemicellulose fibers of the plant cell walls. This solid phase can advantageously be exploited in various applications, in particular in animal nutrition. The aqueous liquid phase obtained at the end of said solid/liquid separation step is composed mainly of water (at least 90% by weight), of sugars, in particular in the form of polysaccharides (advantageously from 0.2% to 4% by weight), and of ferulic acid (advantageously from 10 to 10,000 ppm). Said aqueous phase is basic and has a pH advantageously greater than 9.

In accordance with the process of the invention, said liquid phase obtained after solid/liquid separation according to said step 1) is subjected to a step of selective separation of the polysaccharides dissolved in said liquid phase (step 2). This separation step results in the production of, on the one hand, an aqueous fraction consisting essentially of polysaccharides and, on the other hand, an aqueous fraction comprising ferulic acid. The fraction consisting essentially of polysaccharides is such that the polysaccharides represent at least 90% by weight of the compounds of said fraction other than water. Said selective separation step is advantageously carried out by liquid chromatography, by liquid/liquid extraction, by selective adsorption of the polysaccharides, or by ultrafiltration, very preferably by ultrafiltration. As regards the liquid chromatography, size exclusion chromatography (use of SRT® SEC phases from the company Sepax Technologies, for example) carried out in batchwise mode or in continuous mode with an implementation of simulated moving bed (SMB) type is advantageous. As regards the liquid/liquid extraction, aprotic polar solvents considered to be harmless to the health, in particular ethyl acetate, make it possible to enrich the organic fraction with polysaccharides.

Preferably, said step of selective separation of the polysaccharides is carried out by ultrafiltration by means of an organic or inorganic membrane, preferentially an inorganic membrane. Said membrane is, for example, ceramic or polymeric in nature. Said membrane used for carrying out said ultrafiltration step 2) has pores of which the diameter is between 2 nm and 0.1 μm. It has a cut-off threshold, defined as being the size starting from which the molecules are entirely retained by the membrane, of between 15,000 g/mol and 300,000 g/mol. Advantageously, the cut-off threshold can be between 35,000 g/mol and 300,000 g/mol, preferably between 50,000 g/mol and 300,000 g/mol, preferably between 75,000 g/mol and 300,000 g/mol, and even more preferably between 100,000 g/mol and 300,000 g/mol. The cut-off threshold of the membrane can advantageously be at least 50,000 g/mol.

Said ultrafiltration step is advantageously carried out at a temperature below 100° C. It is preferentially carried out at a pH of between 5 and 12.

In accordance with step 2) of the process according to the invention, the ultrafiltration membrane retains the organic molecules, in particular the polysaccharides, of molar mass greater than 15,000 g/mol present in the liquid phase resulting from the solid/liquid separation and allows an aqueous fraction comprising the ferulic acid in ferulate form, or in the form of a fluidic acid/ferulate mixture, to pass through (permeate). The retentate is an aqueous stream in which the compounds (other than water) are predominantly the polysaccharides, which represent at least 90% by weight, preferably at least 95%, of all the compounds constituting the retentate, other than water. At least 90% by weight, preferably at least 95% by weight and even more preferably at least 98% by weight, of the polysaccharides initially present in the aqueous liquid phase resulting from the solid/liquid separation are retained by the ultrafiltration membrane. Said polysaccharides present in the retentate at the end of the ultrafiltration step are advantageously exploited in various applications, in particular in animal nutrition.

Said aqueous fraction consisting essentially of polysaccharides, obtained at the end of said selective separation step, preferentially the ultrafiltration retentate of step 2), is advantageously concentrated by nanofiltration or reverse osmosis so as to give a retentate which is richer in polysaccharides and a permeate consisting very predominantly of water (>99% by weight) that can be recycled to the plant material treatment step, preferentially the alkaline decoction step.

In accordance with optional step 3) of the process according to the invention, the aqueous fraction comprising the ferulic acid is polysaccharide-depleted, resulting from the step of selective separation of the polysaccharides, preferentially the permeate resulting from said ultrafiltration step is subjected to a concentration step (step 3) so as to produce a concentrated ferulic acid stream and a purified aqueous stream. The ferulic acid concentration in said concentrated stream resulting from the concentration step is advantageously at least twice that of the aqueous fraction resulting from said step 2), in which the ferulic acid is present.

Said concentration step advantageously consists in carrying out either an evapoconcentration step, or a membrane separation step, in particular by nanofiltration or by reverse osmosis.

According to a first preferred embodiment of said step 3) of the process according to the invention, the permeate resulting from said ultrafiltration step is subjected to a step of concentration by evapoconcentration carried out by means of a scraped-film evaporator, a falling film evaporator or a triple-effect evaporator preferably operating at a pressure below atmospheric pressure. The permeate resulting from the ultrafiltration step is in a concentrate in which the ferulic acid is at least 2 times, or even 4 times, more concentrated than in said permeate, and a distillate consisting of pure water is recovered and can be recycled to the plant material treatment step (step 1), in particular to the alkaline decoction step.

According to a second preferred embodiment of said step 3) of the process according to the invention, the permeate resulting from said ultrafiltration step is subjected to a nanofiltration step carried out by means of an organic or inorganic membrane, preferentially an organic membrane, of which the degree of salt rejection (defined as being equal to the percentage of solute which does not pass through the membrane) is at least equal to 80%, preferably at least equal to 95%, preferentially at least equal to 98%. Said membrane is a commercial membrane. More preferably, said membrane used for carrying out said nanofiltration step is made up of one or more polymers, for example of polyamides, and has an $MgSO_4$ rejection rate greater than 98%.

According to a third preferred embodiment of said step 3) of the process according to the invention, the permeate resulting from said ultrafiltration step is subjected to a reverse osmosis step carried out by means of a membrane of which the pore diameter is between 0.1 and 1 nm. An organic or inorganic membrane, preferentially an organic membrane, is used. Said membrane is a commercial membrane. More preferably, said membrane used for carrying out said nanofiltration step is made up of one or more polymers, for example of polyamides, and has an $MgSO_4$ rejection rate greater than 80%, preferably greater than 98%, preferentially greater than 99%.

Said membrane separation step, carried out by nanofiltration or reverse osmosis ($2^{nd}$ and $3^{rd}$ embodiments described), is advantageously carried out at a temperature below 60° C. It is preferentially carried out at a pH less than 9. Thus, depending on the pH at which said step 2) of selective separation of the polysaccharides is carried out, the pH can be adjusted prior to said concentration step 3).

In accordance with the second and third preferred embodiments of said step 3) of the process according to the invention, the membrane performing the membrane separation allows a stream of purified water (permeate) to pass through and retains a concentrated ferulic acid stream (retentate) (in ferulate form or in the form of a mixture of ferulic acid/ferulate). The permeate resulting from said step 3) is composed of purified water of which the content of impurities, in particular of polysaccharides and ferulic acid is infinitesimal, i.e. less than 0.1% by weight (based on the simulated example), or even zero. The permeate based on purified water is advantageously recycled to the plant material treatment step producing the aqueous liquid phase in which the ferulic acid is extracted according to the process of the invention. This thus results in a notable decrease in the consumption of drinking water in the process of treating plant material, in particular for alkaline decoction of plants. The term "concentrated ferulic acid stream", as obtained in the retentate according to said second and third preferred embodiments of said step 3), is intended to mean that the concentration of ferulic acid and/or ferulate is at least doubled after said step 3) has been carried out.

According to the embodiment of the process of the invention in which step 3) is not carried out, the aqueous fraction containing the ferulic acid resulting from said step 2) is directly sent to the step of recovery in crystalline solid form, preferentially while subjecting it beforehand to an evapoconcentration treatment.

In accordance with step 4) of the process according to the invention, said ferulic acid-concentrated stream forming the concentrate or the retentate resulting from said step 3) is treated so as to recover the ferulic acid in crystalline solid form.

Preferably, said step of recovering the ferulic acid in solid crystalline form is carried out by crystallization or atomization. Very preferably, said recovery step according to step 4) of the process according to the invention is carried out by crystallization.

The step of recovering the ferulic acid in solid form, preferably the crystallization step, is preferentially preceded by a step of treating said ferulic acid-concentrated stream consisting in acidifying said concentrated stream or consisting of a step of adsorption of said concentrated stream, the ferulic acid being in ferulate form or in the form of a mixture of ferulic acid/ferulate.

As regards a treatment, prior to the crystallization, by acidification, any inorganic acid is suitable, in particular sulfuric acid, phosphoric acid or hydrochloric acid. The acidification is carried out so as to obtain a ferulic acid stream having a pH of less than 7, preferentially less than 5.

As regards a treatment, prior to the crystallization, by adsorption, said ferulic acid-concentrated stream resulting from said step 3) is brought into contact with an adsorbent material capable of adsorbing onto its surface the ferulic acid and/or the ferulate. Among the adsorbent materials advantageously used in the process of the invention, mention may particularly be made of active carbons and polymer, ion-exchange, adsorbent or size-exclusion resins. Said adsorbent material is advantageously placed either in a stirred reactor or in a column. Said adsorption step is advantageously carried out at a temperature below 40° C. When the adsorption is complete, the adsorbent material is recovered by filtration or regenerated by elution in a column so as to recover the ferulic acid. Preferably, an alcohol, in particular ethanol, or a salt is used to elute the ferulic acid. The composition of said ferulic acid-concentrated stream also directs the choice of the eluent. When the eluent is a salt and, consequently, the ferulic acid is in an aqueous fraction, said aqueous fraction is acidified so that the ferulic acid precipitates. When the eluent is an alcohol, the alcoholic fraction(s) is (are) evaporated so as to recover the ferulic acid in solid form. The ferulic acid thus recovered has a purity that is insufficient for it to be subsequently used as starting material in various processes requiring the use of highly pure reagents. Thus, the ferulic acid is subjected to a recrystallization step in order to increase its purity. Said recrystallization step is advantageously carried out from water.

The crystallization or recrystallization of the ferulic acid in accordance with step 4) of the process according to the invention is carried out by cooling or concentrating the medium in which the ferulic acid is present.

The crystallization by cooling, to a temperature preferentially between 1° C. and 10° C., results in the formation of ferulic acid crystals. The ferulic acid crystals are then advantageously filtered off, washed and then dried. The crystallization is carried out in equipment conventionally used, such as in stirred reactors (known as crystallizers) with internal exchangers and/or circulation of a heat-transfer fluid in a jacket. The crystalline ferulic acid is advantageously dried at a temperature of between 50 and 100° C. Said drying is carried out according to techniques well known to those skilled in the art, for example using contact dryers at atmospheric pressure or under reduced pressure, or convective dryers with air or an inert gas. The ferulic acid can also be dried according to the fluidized-bed technique. The mother liquors and washing waters, harvested at the end of crystallization, are advantageously sent to a purification plant in order to be treated and/or purified.

The crystallization by concentration generally consists in evaporating the water in which the ferulic acid is present. This evaporation step is generally carried out under vacuum. It is carried out according to practices well known to those skilled in the art.

At the end of the implementation of the process according to the invention, the natural ferulic acid obtained has a high purity, generally greater than 95% and even more preferably greater than 99%.

The highly pure ferulic acid thus obtained is advantageously used in a biofermentation process in order to produce natural vanillin in the presence of microorganisms, for example the *Streptomyces setonii* strain. The implementation of such a process for producing natural vanillin from ferulic acid and in the presence of such a strain is described in patents EP 0 761 817 and EP 0 885 968 and results in a high vanillin yield. A subject of the invention is also a process for producing natural vanillin, comprising:
- the extraction of ferulic acid present in an aqueous phase, obtained by treatment of at least one plant material, and also containing polysaccharides, as previously described, and
- the conversion of the ferulic acid thus obtained into natural vanillin by means of a biofermentation process in the presence of microorganisms.

FIG. 1 represents an overall sequence integrating the preferred variants of the process according to the invention, in particular with the use of spent corn grains for the plant material to be treated, treatment by alkaline decoction in order to release the ferulic acid and the polysaccharides from the spent corn grain, separation of the polysaccharides by ultrafiltration and then concentration of the ferulic acid by nanofiltration. The diagram of FIG. 1 also shows the purification of the ultrafiltration retentate by nanofiltration in order to concentrate the polysaccharides, subsequently exploited in animal nutrition. This diagram also shows that it is advantageous, in the implementation of the process according to the invention, to recycle the purified aqueous streams resulting from the nanofiltration steps to the alkaline decoction step.

The invention is illustrated by means of the following examples.

Example 1 (Invention)

Spent corn grains (residues from the starch industry) are introduced into the feed of a twin-screw extruder (Battenfield-Cincinnati BEX2-28D) at a flow rate of 50 kg/h. The twin-screw extruder comprises six compartments in addition to the feed section and is heated to a temperature of 100° C. The six compartments represent a sequence of conveying elements, blending elements, pressure counter-threads and a washing zone at the end of the twin screw. A solution of sodium hydroxide at 10% by weight is introduced on the second compartment of the extruder at a flow rate of 25 kg/h. A stream of washing water is introduced on the final compartment at a flow rate of 400 kg/h. The resulting alkaline decoction stream, exiting the twin-screw extruder, is recovered in a 5 m$^3$ storage tank where it is brought back to ambient temperature.

The aqueous alkaline decoction stream is continuously centrifuged using a plate centrifuge of Flottweg® type in order to separate the residual solids in suspension from the liquid phase containing the dissolved polysaccharides and ferulic acid. A clarified aqueous liquid phase containing approximately 600 ppm of ferulic acid in sodium ferulate form and approximately 5000 ppm of high-molecular-weight (greater than 3000 g/mol) polysaccharides is thus obtained.

10 kg of clarified aqueous liquid phase originating from the alkaline decoction and containing 6.1 g of ferulic acid and 49 g of sugars in the form of polysaccharides are taken.

The pH of this stream is equal to pH=11.3. The clarified stream is brought to pH=7 by adding sulfuric acid and is then treated on a commercial ceramic ultrafiltration membrane (Kerasep® BX 300KD) having a monolithic support based on $TiO_2$—$Al_2O_3$ and an active layer based on $ZrO_2$—$TiO_2$ having a cut-off threshold of 300,000 g/mol, at a temperature of 50° C. in order to separate the polysaccharides having a mass of greater than 300,000 g/mol which remain in the retentate and the ferulic acid which passes into the permeate in ferulate form. 3 kg of retentate containing 48.5 g of sugars (polysaccharides) and 1.1 g of ferulic acid are harvested. 7 kg of ultrafiltration permeate containing 5 g of ferulic acid are collected. The permeate is introduced onto an Alfa Laval NF 99 commercial nanofiltration membrane. The nanofiltration membrane used is a polyamide spiral membrane which has a surface area of 0.34 m² with a degree of $MgSO_4$ rejection at 25° C. of at least 98%. It has a cut-off threshold of between 150 g/mol and 300 g/mol at a temperature of 50° C. This treatment makes it possible to obtain a permeate corresponding to a stream of purified water: 5.75 kg containing 130 ppm of ferulic acid, directly reusable in the step of alkaline decoction of the spent corn grain and a retentate corresponding to a concentrated ferulic acid stream: 1.25 kg containing 4.25 g of ferulic acid.

The retentate recovered in the nanofiltration step is acidified to pH=3-4 by adding sulfuric acid and then cooled to 2° C. in order to cause the ferulic acid to precipitate. The solid is filtered off and then washed 3 times with water to give, after drying, 4 g of 98%-pure ferulic acid. The overall yield of the extraction of ferulic acid contained in the clarified aqueous phase from alkaline decoction of the spent corn grain is equal to 65.5%.

The ultrafiltration retentate containing the polysaccharides can also be concentrated by nanofiltration to give a permeate corresponding to a stream of purified water containing approximately 100 ppm of ferulic acid which can be recycled to the alkaline decoction step, and a retentate corresponding to a stream of concentrated polysaccharides directly exploitable in animal nutrition or as a mixture with the solid residues separated after the alkaline decoction step.

The invention claimed is:

1. A process for extraction of ferulic acid from at least one plant material containing ferulic acid and-polysaccharides, comprising:
   1) treating said plant material to form a solid phase and an aqueous liquid phase, said aqueous liquid phase comprising ferulic acid and/or salt thereof and polysaccharides,
   2) selectively separating polysaccharides from the liquid phase and recovering a polysaccharide-depleted aqueous liquid fraction that comprises ferulic acid and/or salt thereof from the liquid phase, wherein said step of selective separation of the polysaccharides is carried out, without the addition of organic solvent, by selective adsorption of the polysaccharides, or by ultrafiltration,
   3) optionally, concentrating the aqueous liquid fraction to recover a concentrated ferulic acid stream that comprises ferulic acid and/or salt thereof from the liquid fraction,
   4) if the aqueous liquid fraction or, if the optional step 3 of concentrating is performed, the concentrated ferulic acid stream comprises a salt of ferulic acid, converting the salt of ferulic acid to ferulic acid, and
   5) recovering ferulic acid, in solid form, from the aqueous liquid fraction or, if the optional step 3 of concentrating is performed, from the concentrated ferulic acid stream.

2. The process as claimed in claim 1, wherein said plant material is selected from the group consisting of wheat bran, rice bran, corn bran, oat bran, spent corn grains, bagasse, beetroot pulp, residue from refining rice bran oil, and mixtures thereof.

3. The process as claimed in claim 1, wherein the step of treating said plant material to form the aqueous liquid and solid phases comprises subjecting the plant material to an alkaline decoction and/or enzymatic treatment.

4. The process as claimed in claim 3, wherein the alkaline decoction comprises heating said plant material in an alkaline solution or an alkaline suspension.

5. The process as claimed in claim 3, wherein the treatment by alkaline decoction is carried out in a twin-screw extruder or a grinder-homogenizer.

6. The process as claimed in claim 1, wherein said aqueous liquid phase formed in step 1 comprises mainly water, sugars, and ferulic acid.

7. The process as claimed in claim 1, wherein the step of selectively separating polysaccharides comprises ultrafiltration, and wherein the ultrafiltration is carried out by means of an organic or inorganic ultrafiltration membrane.

8. The process as claimed in claim 7, wherein said membrane has a cut-off threshold of between 50 000 g/mol and 300 000 g/mol.

9. The process as claimed in claim 1, wherein the step of selective separating polysaccharides comprises ultrafiltration, and wherein the ultrafiltration is carried out at a pH of between 5 and 12.

10. The process as claimed in claim 7, wherein at least 90% by weight of the polysaccharides initially present in the aqueous liquid phase are retained by the ultrafiltration membrane.

11. The process as claimed in claim 1, wherein said concentration step consists in carrying out either an evapo-concentration step, or a membrane separation step by nanofiltration or by reverse osmosis.

12. The process as claimed in claim 11, wherein the membrane separation step is carried out at a pH of less than 9.

13. The process as claimed in claim 11, wherein the concentration of ferulic acid and/or salt thereof is at least doubled after said step 3) has been carried out.

14. The process as claimed in claim 1, wherein said recovery step according to step 4) comprises crystallization of ferulic acid.

15. The process as claimed in claim 14, wherein the crystallization of the ferulic acid is preceded by acidifying said concentrated ferulic acid stream or adsorption of said concentrated ferulic acid stream.

16. A process for producing natural vanillin, comprising biofermenting ferulic acid obtained by the process claimed in claim 1.

17. A process for producing natural vanillin, comprising:
   extracting ferulic acid from at least one plant material as claimed in claim 1, and
   converting the ferulic acid thus obtained into natural vanillin by biofermentation in the presence of microorganisms.

* * * * *